(12) United States Patent
Schubert et al.

(10) Patent No.: US 8,648,002 B2
(45) Date of Patent: Feb. 11, 2014

(54) PROCESS FOR MAKING AND USING METAL ORGANIC FRAMEWORKS BASED ON ALUMINUM, IRON AND CHROMIUM

(71) Applicant: BASF SE, Ludwigshafen (DE)

(72) Inventors: Markus Schubert, Ludwigshafen (DE); Ulrich Müller, Neustadt (DE); Stefan Marx, Zürich (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/734,490

(22) Filed: Jan. 4, 2013

(65) Prior Publication Data

US 2013/0165687 A1   Jun. 27, 2013

Related U.S. Application Data

(62) Division of application No. 12/597,616, filed as application No. PCT/EP2008/054887 on Apr. 23, 2008, now Pat. No. 8,372,779.

(30) Foreign Application Priority Data

Apr. 24, 2007   (EP) .................................... 07106802

(51) Int. Cl.
  *B01J 31/00*   (2006.01)
(52) U.S. Cl.
  USPC .......................................... 502/150; 502/439
(58) Field of Classification Search
  USPC .................................. 502/150, 314, 316, 439
  See application file for complete search history.

(56) References Cited

U.S. PATENT DOCUMENTS

2006/0287190 A1   12/2006   Eddaoudi et al.

FOREIGN PATENT DOCUMENTS

| WO | WO2006/116340 | 11/2006 |
| WO | WO2007/023134 | 3/2007 |
| WO | WO2007/101797 | 9/2007 |

OTHER PUBLICATIONS

International Search Report in international application No. PCT/EP2008/054887, dated Jul. 2, 2009.

Rusanov, Eduard B. et al., "A Topology Paradigm for Metal-Organic Zeolites", Angewandte Chemie International Edition, vol. 42, No. 22, pp. 2499-2501, (Jun. 5, 2003).
Moulton, Brian et al., "Crystal Engineering of a Nanoscale Kagome Lattice", Angewandte Chemie International Edition, vol. 41, No. 15, pp. 2821-2824, (Aug. 2, 2002).
Barthelet, K. et al., "$V^{III}$(OH){$O_2C$—$C_6H_4$—$CO_2$}.(H$O_2$C—$C_6H_4$—$CO_2$H)$_x$(DMF)$_y$(H$_2$O)$_z$ (or MIL-68), a new vanadocarboxylate with a large pore hybrid topology : reticular synthesis with infinite inorganic building blocks?", Chemical Communications, vol. 2004, No. 5, pp. 520-521, (Feb. 5, 2004).
Eddaoudi, Mohamed et al., "Geometric requirements and examples of important structures in the assembly of square building blocks", Proceedings of the National Academy of Sciences of USA, PNAS, vol. 99, No. 8, pp. 4900-4904, (Jan. 1, 2002).
Jhung, Sung Hwa et al., "Microwave Synthesis of Chromium Terephthalate MIL-101 and Its Benzene Sorption Ability", Advanced Materials, vol. 19, No. 1, pp. 121-124, (Dec. 7, 2006).
Latroche, Michel et al., "Hydrogen Storage in the Giant-Pore Metal-Organic Frameworkds MIL-100 and MIL-101", Angewandte Chemie, vol. 118, No. 48, pp. 8407-8411, (Nov. 23, 2006).
Ferey, G. et al., "A Chromium Terephthalate-Based Solid with Unusually Large Pore Volumes and Surface Area", Science, vol. 309, pp. 2040-2042 and 1, (Sep. 23, 2005).
Sonnauer, Andreas et al., "Giant Pores in a Chromium 2,6-Naphthalenedicarboxylate Open-Framework Structure with MIL-101 Topology", Angewandte Chemie International Edition, vol. 48, No. 21, pp. 3791-3794, (Feb. 4, 2009).
Whitfield, Tabatha R. et al., "Metal-organic frameworks based on iron oxide octaherdal chains connected by benzenedicarboxylate dianions", Solid State Sciences, Elsevier, vol. 7, No. 9, pp. 1096-1103, (Jan. 1, 2005).
Liu, Yunling et al., "Molecular building blocks approach to the assembly of zeolite-like metal-organic frameworks (ZMOFs) with extra-large cavities", Chem. Commun., pp. 1488-1490, (2006).
Loiseau, Thierry et al., "A Rationale for the Large Breathing of the Porous Aluminum Terephthalate (MIL-53) Upon Hydration", Chem. Eur. J., vol. 10, pp. 1373-1382, (2004).
Bourrelly, Sandrine et al., "Different Adsorption Behaviors of Methane and Carbon Dioxide in the Isotypic Nanoporous Metal Terephthalates MIL-53 and MIL-47", J. Am. Chem. Soc., vol. 127, No. 39, pp. 13519-13521, (2005).

*Primary Examiner* — Edward Johnson
(74) *Attorney, Agent, or Firm* — Oblon, Spivak, McClelland, Maier & Neustadt, L.L.P.

(57) ABSTRACT

The present invention relates to a porous metal organic framework comprising a bidentate organic compound coordinated to a metal ion selected from the group of metals consisting of Al, Fe and Cr, with the bidentate organic compound being derived from a dicarboxylic acid, wherein the framework has a structure whose projection along [001] has a pattern in which each side of a hexagon is bounded by a triangle. The present invention further relates to shaped bodies and a process for preparing the porous metal organic framework and its use.

15 Claims, 2 Drawing Sheets

PROCESS FOR MAKING AND USING METAL ORGANIC FRAMEWORKS BASED ON ALUMINUM, IRON AND CHROMIUM

This application is a Divisional of U.S. application Ser. No. 12/597,616, filed on Dec. 4, 2009, which is a National Stage of PCT/EP2008/054887, filed Apr. 23, 2008.

DESCRIPTION

The present invention relates to porous metal organic frameworks, shaped bodies comprising these and a process for preparing them and their use.

Porous metal organic frameworks are known from the prior art. They are notable, in particular, for their porosity and can frequently be employed in applications comparable to those known for inorganic zeolites.

Metal organic frameworks usually comprise an at least bidentate organic compound which is coordinated to a metal ion and together with the metal ion forms the skeleton of the metal organic framework.

Appropriate choice of metal and/or organic compound makes optimization for the desired field of application possible. Here, for example, the choice of organic compound can exert an influence on the pore distribution. In addition, the metal can make a contribution in adsorption processes.

However, reaction conditions in the preparation of metal organic frameworks and auxiliaries used in the reaction can also influence the framework structure.

Thus, for example, zeolite-like metal organic frameworks are produced by Y. Liu et al., Chem. Commun. 14 (2006), 1488-1490, with the aid of structure-directing agents. Further such frameworks are described in WO-A 2006/116340.

There is thus a continual need to provide specific metal organic frameworks which have, in particular, extraordinary properties which are attributable to, in particular, specific preparative methods.

An interesting metal is aluminum since comparatively robust metal organic frameworks can be obtained because of strong coordinate bonds. In addition, because of its octahedral coordination, the $Al^{3+}$ ion is in principle suitable for building up three-dimensional frameworks. Furthermore, the salts of aluminum which can be used as starting materials are readily available and inexpensive. Owing to their similar structure, metal organic frameworks based on iron and chromium are also of interest in addition to those based on aluminum.

A particularly interesting metal organic framework is aluminum terephthalate. This is described by T. Loiseau et al., Chem. Eur. J. 10 (2004), 1373-1382. A conventional preparation gives a base structure in which parallel —Al—(OH)—Al—(OH)— chains are crosslinked into the second and third dimension of the dicarboxylic linker, so that they span one-dimensional channels having a diamond-shaped cross section. The base structure is known in the literature as "MIL-53". The crystal system is, (in the dry "ht" form) orthorhombic and the space group is Imma. The same structure is produced in the conventional preparation of iron terephthalate and chromium terephthalate (T. R. Whitfield et al., Solid State Sciences 7 (2005), 1096-1103; S. Bourrelly et al., J. Am. Chem. Soc. 127 (2005), 13519-13521).

Despite the known metal organic frameworks, there is a need for alternative frameworks which have superior properties, especially in respect of the storage and separation of gases.

It is therefore an object of the present invention to provide such frameworks and a process for preparing them.

The object is achieved by a porous metal organic framework comprising a bidentate organic compound coordinated to a metal ion selected from the group of metals consisting of Al, Fe and Cr, with the bidentate organic compound being derived from a diacarboxylic acid, wherein the framework has a structure whose projection along [001] has a pattern in which each side of a hexagon is bounded by a triangle.

The object is likewise achieved by a process for preparing a porous metal organic framework according to the invention, which comprises the step reaction of a reaction mixture comprising at least one compound of a metal selected from the group consisting of Al, Fe and Cr and the bidentate organic compound or a salt thereof in the presence of an auxiliary having at least one deprotonatable group in an organic solvent at a predetermined temperature and a predetermined pressure.

It has been found that the above-described production process using an auxiliary forms novel metal organic frameworks which have a structure different from the conventionally prepared known structures made up of the same metals and organic compounds.

In particular, it has surprisingly been found that in the presence of an auxiliary a structure known as "MIL-68" for $V^{III}$-comprising metal organic frameworks is formed, with the structure being obtained spontaneously in these frameworks. Vanadium terephthalate is described by K. Barthelet et al., Chem. Commun. 2004, 520-521. Here, a structure whose projection along [001] has a pattern in which each side of a hexagon is bounded by a triangle is found.

The present invention is described in more detail below.

Figure 1:
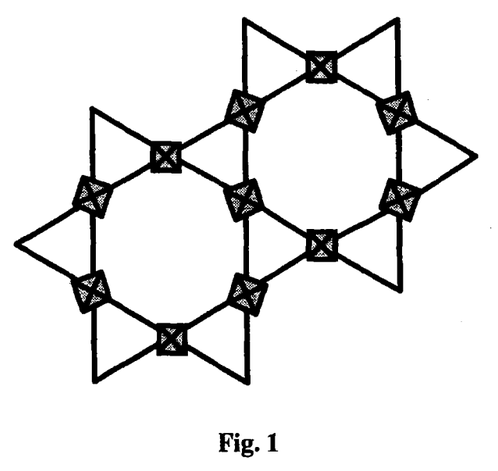
FIG. 1 schematically shows the above-described pattern, with the octahedra depicted in FIG. 1 representing the octahedrally coordinated metal centers.

FIG. 1 shows the above-described pattern purely schematically. A more detailed depiction is shown in FIG. 2 on page 520 of K. Barthelet et al., Chem. Commun. 2004, 520-521.

Particularly the case of aluminum terephthalate, the structure of the corresponding porous metal organic framework of the invention can be recognized by the X-ray diffraction pattern (XRD) having a main reflection in the range 4°<2Θ<6°, preferably in the range 4.5°<2Θ<5.5°.

Here, the diffraction pattern can be determined as follows: the sample is installed as powder in the sample container of a commercially available instrument (Siemens D-5000 diffractometer or Bruker D8-Advance). As radiation source, use is made of Cu-Kα radiation using variable primary and secondary orifice plates and a secondary monochromator. The signal is detected by means of a scintillation detector (Siemens) or a Solex semiconductor detector (Bruker). The measurement range for 2Θ is typically from 2° to 70°. The angle step is 0.02° and the measurement time per angle step is typically from 2 to 4 seconds. In the evaluation, reflections are distinguished from the background noise by an at least 3-times higher signal strength. An area analysis can be carried out manually by drawing a baseline for the individual reflections. As an alternative, programs such as "Topas-Profile" from Bruker can be used, in which case the fitting to the background is preferably carried out automatically by means of a 1st order polynomial in the software.

The structure of the aluminum terephthalate framework of the invention has an orthorhombic unit cell and has the space group Cmcm.

The abbreviations used for the space groups are known to those skilled in the art and are standardized. Reference may be made, for example, to the Internet page of the International Union of Crystallography (http://www.iucr.org/iucr-top/it/index.html).

The metal component of the framework of the present invention is selected from the group of metals consisting of Al, Fe and Cr. Preference is given to Al. Particular mention should here be made of the trivalent ions.

In addition, the metal organic framework of the invention comprises a bidentate organic compound derived from a dicarboxylic acid.

For the purposes of the present invention, the term "derived" means that the bidentate organic compound is present in partly deprotonated or completely deprotonated form or as a sulfur analogue in which one or both carboxylic acid functions have been replaced by the functional group —C(=O)SH or its tautomer or C(=S)SH in the framework. Furthermore, the bidentate organic compound can comprise further substituents such as —OH, —NH$_2$, —OCH$_3$, —CH$_3$, —NH(CH$_3$), —N(CH$_3$)$_2$, —CN and halides.

For example, the bidentate organic compound is derived from a dicarboxylic acid such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecane-dicarboxylic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diamino-phenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octa-dicarboxylic acid, pentane-3,3-carboxylic acid, 4,4'-diamino-1,1'-biphenyl-3,3'-di-carboxylic acid, 4,4'-diaminobiphenyl-3,3'-dicarboxylic acid, benzidine-3,3'-dicarboxylic acid, 1,4-bis(phenylamino)benzene-2,5-dicarboxylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran 250-dicarboxylic acid, 1,4-bis(carboxy-methyl)piperazine-2,3-dicarboxylic acid, 7-chloroquinoline-3,8-dicarboxylic acid, 1-(4-carbm)phenyl-3-(4-chloro)phenylpyrazoline-4,5-dicarboxylic acid, 1,4,5,6,7,7-hexa-chloro-5-norbornene-2,3-dicarboxylic acid, phenylindandicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2,-benzoylbenzene-1,3-dicarboxylic acid, 1,3-di-benzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxy-benzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diamino(diphenyl ether)diimidedicarboxylic acid, 4,4'-diaminodiphenyl-methanediimidedicarboxylic acid, 4,4'-diamino(diphenyl sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenecarboxylic acid, 8-sulfo-2,3-naphthalenedicarboxylic acid, anthracene-2,3-dicarboxylic acid, 2',3'-diphenyl-p-terphenyl-4,4'''-dicarboxylic acid, (diphenyl ether)-4,4'-dicarboxylic acid, imidazole-4,5-dicarboxylic acid, 4(1 H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptadicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonen-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4, 11-dicarboxylic acid, 7-chloro-3-methylquinoline-6,8-dicarboxylic acid, 2,4-dichlorobenzophenon-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrol-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarbmlic acid, 5,6-dehydronorbornane-2,3-dicarboxylic acid, 5-ethyl-2,3-pyridinedicarboxylic acid or camphordicarboxylic acid.

The at least bidentate organic compound is more preferably one of the dicarboxylic acids mentioned by way of example above as such.

Particular preference is given to aromatic dicarboxylic acids having from 6 to 14 ring atoms which can be carbon or nitrogen. However, the ring preferably does not have any heteroatoms. The at least one organic compound is particularly preferably derived from a benzenedicarboxylic or naphthalenedicarboxylic acid. In particular, the compound is at least one of these dicarboxylic acids as such.

Particular mention may here be made of 1,2-benzenedicarboxylic acid (phthalic acid), 1,3-benzenedicarboxylic acid (isophthalic acid), 1,4-benzenedicarboxylic acid (terephthalic acid), 2,6-naphthalenedicarboxylic acid, 1,4-naphthalenedicarboxylic acid and 1,5-naphthalenedicarboxylic acid as dicarboxylic acid. Very particular preference is given to terephthalic acid.

A particularly preferred metal organic framework according to the invention is aluminum terephthalate.

The metal organic framework according to the invention can be present in powder form or as agglomerate.

The porous metal organic framework according to the invention can be used as such in powder form or is converted into a shaped body.

Accordingly, a further aspect of the present invention provides for the porous metal organic framework of the invention to be present as powder.

A further aspect of the present invention is accordingly a shaped body comprising the porous metal organic framework of the invention.

The production of shaped bodies comprising metal organic frameworks is described, for example, in WO-A 03/102000.

Preferred methods of producing shaped bodies are extrusion or tableting. In the production of shaped bodies, the framework can be admixed with further materials such as binders, lubricants or other additives which are added during production. It is likewise conceivable for the framework to have further constituents such as absorbents such as activated carbon or the like.

The possible geometries of the shaped bodies are subject to essentially no restrictions. Examples of shapes are, inter alia, pellets such as circular pellets, pills, spheres, granules, extrudates such as rods, honeycombs, grids or hollow bodies.

To produce these shaped bodies, all suitable processes are possible in principle. The following procedures are particularly preferred:

kneading/pan milling of the framework either alone or together with at least one binder and/or at least one pasting agent and/or at least one template compound to give a mixture; shaping of the resulting mixture by means of at least one suitable method such as extrusion; optional washing and/or drying and/or calcination of the extrudate; optional finishing treatment.

Tableting together with at least one binder and/or another auxiliary.

Application of the framework to at least one porous or nonporous support material. The material obtained can then be processed further to produce a shaped body by the above-described method.

Application of the framework to at least one porous or nonporous substrate.

Kneading/pan milling and shaping can be carried out by any suitable method, as described, for example, in Ullmann's Enzyklopadie der Technischen Chemie 4, 4th edition, volume 2, p. 313 ff. (1972).

Kneading/pan milling and/or shaping can, for example, be carried out by means of a piston press, roller press in the presence or absence of at least one binder material, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or at superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder which can in principle be any chemical compound which ensures a viscosity of the composition to be kneaded and/or shaped which is desired for kneading and/or shaping. Accordingly, binders can, for the purposes of the present invention, be either viscosity-increasing or viscosity-reducing compounds.

Preferred binders are, for example, aluminum oxide or binders comprising aluminum oxide, as described, for example, in WO 94/29408, silicon dioxide, as described, for example, in EP 0 592 050 A1, mixtures of silicon dioxide and aluminum oxide, as described, for example, in WO 94/13584, clay minerals as described, for example, in JP 03-037156 A, for example montmorillonite, kaolin, bentonite, halloysite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetralkoxytitanates such as tetramethoxytitanate, tetraethoxytitanate, tetrapropoxytitanate, tetrabutoxytitanate, or, for example, trialkoxytitanates, such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols, amphiphilic substances and/or graphite.

As viscosity-increasing compound, it is possible to also use, if appropriate in addition to the abovementioned compounds, for example, an organic compound and/or a hydrophilic polymer such as cellulose or a cellulose derivative such as methylcellulose and/or a polyacrylate and/or a polymethacrylate and/or a polyvinyl alcohol and/or a polyvinyl pyrrolidone and/or a polyisobutene and/or a polytetrahydrofuran and/or a polyethylene oxide.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or in admixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds, e.g. calcium carbonate. Such further additives are described, for instance, in EP 0 389 041 A1, EP 0 200 260 A1 or WO 95/19222.

The order of addition of the additives such as template compound, binder, pasting agent, viscosity-increasing substance in shaping and kneading is in principle not critical.

In a further preferred embodiment, the shaped body obtained after kneading and/or shaping is subjected to at least one drying step which is generally carried out at a temperature in the range from 25 to 500° C., preferably in the range from 50 to 500° C. and particularly preferably in the range from 100 to 350° C. It is likewise possible to carry out drying under reduced pressure or under a protective gas atmosphere or by spray drying.

In a particularly preferred embodiment, at least one of the compounds added as additives is at least partly removed from the shaped body during this drying process.

The metal organic framework of the invention comprises pores, in particular micropores and/or mesopores. Micropores are defined as pores having a diameter of 2 nm or less and mesopores are defined by a diameter in the range from 2 to 50 nm (Pure & Appl. Chem. 57 (1985) 603-619). The presence of micropores and/or mesopores can be checked by means of sorption measurements which determine the uptake capacity of the metal organic frameworks for nitrogen as 77 kelvin (Langmuir method) in accordance with DIN 66131 and/or DIN 66134.

The specific surface area, calculated according to the Langmuir model (DIN 66131, 66134), of the metal organic framework of the invention in powder form is preferably at least 1000 $m^2/g$, more preferably at least 1200 $m^2/g$, more preferably at least 1400 $m^2/g$, even more preferably at least 1600 $m^2/g$, even more preferably at least 1650 $m^2/g$.

Shaped bodies comprising the metal organic framework of the invention can have a lower specific surface area; but preferably at least 500 m²/g, more preferably at least 600 m²/g, even more preferably at least 700 m²/g, in particular at least 800 m²/g.

The porous metal organic framework of the invention can be obtained by reaction of a reaction mixture comprising at least one compound of a metal selected from the group consisting of Al, Fe and Cr and the bidentate organic compound or a salt thereof in the presence of an auxiliary having at least one deprotonatable group. The reaction takes place in an organic solvent at a predetermined temperature and a predetermined pressure.

As organic component of the porous metal organic framework of the invention, use is made of a dicarboxylic acid which can be reacted with a metal compound. It is likewise possible to use derivatives of the dicarboxylic acid. Thus, for example, it is conceivable to use the dicarboxylic acid in the form of its salt. The salt, in which the dicarboxylic acid is present as completely or partly deprotonated anion, can have any suitable cation.

Such cations can be, for example, monovalent or divalent, preferably monovalent, metal ions. Examples are, in particular, sodium and potassium salts. It is likewise possible to use cations of ammonium compounds. Here, particular mention may be made of ammonium itself and also alkylammonium cations.

The metal compound can be produced by anodic oxidation of the corresponding metal. In such a case, the porous metal organic framework of the invention is prepared by an at least partly electrochemical route. Processes for the electrochemical preparation of porous metal organic frameworks are described in WO-A 2005/049892. The metal compound for the porous metal organic framework of the invention can also be produced in this way.

In the electrochemical preparation of the porous metal organic framework of the invention, cathodic redeposition of the metal ion is preferably at least partly prevented by means of at least one of the following measures:
(i) use of an electrolyte which promotes cathodic formation of hydrogen;
(ii) addition of at least one compound which leads to cathodic depolarization;
(iii) use of a cathode having a suitable hydrogen overvoltage.

The process can be carried out in an undivided electrolysis cell. Especially suitable cells are gap cells or stacked plate cells. These can be connected in a bipolar fashion. Suitable reaction media are, for example, methanol, ethanol, dimethylformamide, diethylformamide and mixtures of two or more of these solvents.

Furthermore, an electrolyte salt or a plurality of electrolyte salts can be present in the reaction mixture. Here, the electrolyte salt can have a quaternary ammonium ion as cation component and an alkoxysulfate ion as anion component. The total solids content should be greater than or equal to 0.5% by weight.

The reaction in the process of the invention for preparing the metal organic framework of the invention can also be carried out by a classical route. Here, the metal compound is typically a metal salt.

The metal salt can be in the form of an alkoxide, acetonate, halide, sulfite, as salt of an organic or inorganic, oxygen-comprising acid or a mixture thereof.

An alkoxide is, for example, a methoxide, ethoxide, n-propoxide, i-propoxide, n-butoxide, i-butoxide, t-butoxide or phenoxide.

An acetonate is, for example, acetylacetonate.

A halide is, for example, chloride, bromide or iodide.

An organic, oxygen-comprising acid is, for example, formic acid, acetic acid, propionic acid or another alkylmonocarboxylic acid.

An inorganic, oxygen-comprising acid is, for example, sulfuric acid, sulfurous acid, phosphoric acid or nitric acid.

The metal compound can, if appropriate, have water of hydration, which is preferred.

Particular preference is given to the hydrates of the chloride, nitrate and sulfate as metal compound.

The process of the invention takes place in the presence of an auxiliary which has at least one deprotonatable group. This is necessary in order to obtain the less thermodynamically favorable structure according to the invention for the metal organic frameworks of the invention rather than the "MIL-53" structure known from the prior art.

Suitable deprotonatable groups are, in particular, the hydroxy group, the amino group, the carboxyl group, the sulfonic acid group, the phosphonic acid group. Here, the carboxylic acid and the sulfonic acid group are preferred.

The auxiliary preferably has at least one heteroatom selected from the group consisting of nitrogen and sulfur. In addition, preference is given to at least one aromatic substructure being present.

The auxiliary preferably has a molar mass in the range from 140 to 1000 g/mol. The molar mass is more preferably at least 200 g/mol, even more preferably at least 300 g/mol and in particular more than 400 g/mol.

Examples of suitable auxiliaries are 3,5-dihydroxybenzoic acid, 2,5-dihydroxybenzoic acid, mucic acid, glutamine, 4-sulformoylbenzoic acid, 2-mercaptonicotinic acid, calconcarboxylic acid or sulfasalazine.

Particular preference is given to calconcarboxylic acid and sulfasalazine, in particular sulfasalazine.

The reaction in the process of the invention for preparing the porous metal organic framework of the invention is carried out at least in the presence of an organic solvent. Solvothermal conditions can be used here.

For the purposes of the present invention, the term "thermal" refers to a production process in which the reaction to form the porous metal organic framework of the invention is carried out in a pressure vessel which is closed during the reaction and is heated to an elevated temperature so that a pressure is built up within the reaction medium in the pressure vessel as a result of the vapor pressure of the solvent present.

The reaction is preferably not carried out in a water-comprising medium and likewise not under solvothermal conditions.

Accordingly, the reaction in the process of the invention is preferably carried out in the presence of a nonaqueous solvent The reaction is preferably carried out at a pressure of from 1 bar to 16 bar (absolute), preferably from 1 to 3 bar (absolute). However, the pressure is more preferably not more than 1230 mbar (absolute). In particular, the reaction takes place at atmospheric pressure. However, slightly superatmospheric or subatmospheric pressures can occur as a result of the apparatus. For the purposes of the present invention, the term "atmospheric pressure" means the actual atmospheric pressure±150 mbar.

The reaction preferably takes place in a temperature range from 100° C. to 200° C. The temperature is preferably in the range from 110° C. to 170° C. The temperature is more preferably in the range from 120° C. to 150° C.

The reaction mixture can further comprise a base. This serves, in particular, to make the dicarboxylic acid readily soluble. The use of an organic solvent frequently makes it unnecessary to use such a base. Nevertheless, the solvent for the process of the invention can be selected so that it itself has a basic reaction, but this is not absolutely necessary for carrying out the process of the invention.

It is likewise possible to use a base. However, preference is given to not using any additional base.

It is also advantageous for the reaction to take place while stirring, which is also advantageous in the case of a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cycloketones such as cyclohexanone, sulfolene or mixtures thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane which has from 1 to 200 carbon atoms and in which one or more up to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF, DMAc and NMP. Particular preference is given to DMF.

The term "nonaqueous" preferably refers to a solvent which has a maximum water content of 10% by weight, more preferably 5% by weight, even more preferably 1% by weight, more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" encompasses pure solvents and mixtures of different solvents.

Furthermore, the process step of reaction of the at least one metal compound with the at least one bidentate organic compound is preferably followed by a calcination step. The temperature set here is typically above 250° C., preferably from 300 to 400° C.

The calcination step enables the at least bidentate organic compound present in the pores to be removed.

In addition or as an alternative thereto, the removal of the at least bidentate organic compound (ligand) from the pores of the porous metal organic framework can be effected by treatment of the framework formed with a nonaqueous solvent. Here, the ligand is removed in a type of "extraction process" and, if appropriate, replaced by a solvent molecule in the framework.

The treatment is preferably carried out for at least 30 minutes and can typically be carried out for up to 7 days. This can occur at room temperature or elevated temperature. It is preferably carried out at elevated temperature, for example at least 40° C., preferably 60° C. Furthermore, the extraction preferably takes place at the boiling point of the solvent used (under reflux).

The treatment can be carried out in a simple vessel by slurrying and stirring the framework. It is also possible to use extraction apparatuses such as Soxhlet apparatuses, in particular industrial extraction apparatuses.

As solvents, it is possible to use those mentioned above, i.e., for example, $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cycloketones such as cyclohexanone or mixtures thereof.

Preference is given to methanol, ethanol, propanol, acetone, MEK and mixtures thereof.

A very particularly preferred extractant is methanol.

The solvent used for the extraction can be identical or different to that for the reaction of the at least one metal compound with the at least one at least bidentate organic compound. In the "extraction" it is not absolutely necessary but preferred that the solvent is water-free.

The present invention further provides for the use of a porous metal organic framework according to the invention for the uptake of at least one substance for the purposes of its storage, separation, controlled release, chemical reaction or as support.

The at least one substance is preferably a gas or a gas mixture. Liquids are also possible.

In addition, the porous metal organic framework of the invention is suitable for preparing the corresponding metal oxides. Such transformations are described in the International Application number PCT/EP2007/053571. Here, the metal organic framework is heated to above its complete decomposition temperature, so that the metal organic framework which comprises the at least one metal ion forms the metal oxide corresponding to the at least one metal ion or corresponding metal oxide mixtures. The specific surface area of the framework can advantageously be reproduced in the metal oxide (mixture).

The present invention therefore further provides for the use of a metal organic framework for preparing a corresponding metal oxide. For the purposes of the present invention, the term "metal oxide" is used in the interests of simplicity even when a metal oxide mixture is present.

The uses according to the invention of the metal organic framework apply analogously to shaped bodies comprising the framework.

Processes for storage by means of metal organic frameworks in general are described in WO-A 2005/003622, WO-A 2003/064030, WO-A 2005/049484, WO-A 2006/089908 and DE-A 10 2005 012 087. The processes described there can also be used for the metal organic framework of the invention. Preferred gases for storage are methane and hydrogen.

Processes for separation or purification by means of metal organic frameworks in general are described in EP-A 1 674 555, DE-A 10 2005 000938 and in the German patent application number DE-A 10 2005 022 844. The processes described there can also be used for the metal organic framework of the invention. A gas which is preferably separated off is carbon dioxide, in particular from a gas mixture which further comprises carbon monoxide.

If the porous metal organic framework of the invention is used for storage, this is preferably carried out in a temperature range from −200° C. to +80° C. A temperature range from −40° C. to +80° C. is more preferred. A preferred pressure range is from 20 bar to 1000 bar (absolute), in particular from 100 bar to 400 bar.

For the purposes of the present invention, the terms "gas" and "liquid" are used in the interests of simplicity, but gas mixtures and liquid mixtures or liquid solutions are likewise encompassed by the term "gas" or "liquid".

Preferred gases are hydrogen, natural gas, town gas, hydrocarbons, in particular methane, ethane, ethene, acetylene, propane, n-butane and i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon.

The gas is particularly preferably carbon dioxide which is separated off from a gas mixture comprising carbon dioxide. The gas mixture preferably comprises carbon dioxide together with at least $H_2$, $CH_4$ or carbon monoxide. In particular, the gas mixture comprises carbon monoxide in addition to carbon dioxide. Very particular preference is given to mixtures which comprise at least 10 and not more than 45% by volume of carbon dioxide and at least 30 and not more than 90% by volume of carbon monoxide.

A preferred embodiment is pressure swing adsorption using a plurality of parallel adsorber reactors, with the adsorbent bed being made up completely or partly of the material according to the invention. The adsorption phase for the $CO_2$/CO separation preferably takes place at $CO_2$ partial pressure of from 0.6 to 3 bar and a temperature of at least 20° C., but not more than 70° C. To desorb the adsorbed carbon dioxide, the total pressure in the adsorber reactor concerned is usually reduced to values in the range from 100 mbar to 1 bar.

Preference is also given to the use of the framework of the invention for the storage of a gas at a minimum pressure of 100 bar (absolute). The minimum pressure is more preferably 200 bar (absolute), in particular 300 bar (absolute). The gas is in this case particularly preferably hydrogen or methane.

However, the at least one substance can also be a liquid. Examples of such a liquid are disinfectants, inorganic or organic solvents, fuels, in particular gasoline or diesel, hydraulic fluid, radiator fluid, brake fluid or an oil, in particular machine oil. The liquid can also be halogenated aliphatic or aromatic, cyclic or acyclic hydrocarbons or mixtures thereof. In particular, the liquid can be acetone, acetonitrile, aniline, anisol, benzene, benzonitrile, bromobenzene, butanol, tert-butanol, quinoline, chlorobenzene, chloroform, cyclohexane, diethylene glycol, diethyl ether, dimethylacetamide, dimethylformamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or mixtures thereof.

Furthermore, the at least one substance can be an odorous substance.

The odorous substance is preferably a volatile organic or inorganic compound which comprises at least one of the elements nitrogen, phosphorus, oxygen, sulfur, fluorine, chlorine, bromine or iodine or is an unsaturated or aromatic hydrocarbon or a saturated or unsaturated aldehyde or a ketone. More preferred elements are nitrogen, oxygen, phosphorus, sulfur, chlorine, bromine; and particular preference is given to nitrogen, oxygen, phosphorus and sulfur.

In particular, the odorous substance is ammonia, hydrogen sulfide, sulfur oxides, nitrogen oxides, ozone, cyclic or acyclic amines, thiols, thioethers and aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptanoic acid, lauric acid, pelargonic acid) and cyclic or acyclic hydrocarbons comprising nitrogen or sulfur and saturated or unsaturated aldehydes such as hexanal, heptanal, octanal, nonanal, decanal, octenal or nonenal and in particular volatile aldehydes such as butyraldehyde, propionaldehyde, acetaldehyde and formaldehyde and also fuels such as gasoline, diesel (constituents).

The odorous substances can also be fragrances which are used, for example, for producing perfumes. Examples of fragrances or oils which can release such fragrances are: essential oils, basil oil, geranium oil, mint oil, cananga oil, cardamom oil, lavender oil, peppermint oil, nutmeg oil, camomile oil, eucalyptus oil, Rosemary oil, lemon oil, lime oil, orange oil, bergamot oil, muscatel sage oil, coriander oil, cypress oil, 1,1-dimethoxy-2-phenylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethyl vanillin, 2,6-dimethyl-2-octenol, 3,7-dimethyl-2-octenol, tert-butylcyclohexyl acetate, anisyl acetate, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranyl nitrile, cis-3-hexen-1-ol, cis-3-hexenyl acetate, cis-3-hexenyl methyl carbonate, 2,6-dimethyl-5-hepten-1-al, 4-(tricyclo[5.2.1.0]decylidene)-8-butanal, 5-(2,2,3-trimethyl-3-cyclopentenyl)-3-methylpentan-2-ol, p-tert-butyl-alpha-methylhydrocinnamaldehyde, ethyl[5.2.1.0]tricyclodecanecarboxylate, geraniol, citronellol, citral, linalool, linalyl acetate, ionone, phenylethanol and mixtures thereof.

For the purposes of the present invention, a volatile odorous substance preferably has a boiling point or boiling point range below 300° C. The odorous substance is more preferably a readily volatile compound or mixture. In particular, the odorous substance has a boiling point or boiling range below 250° C., more preferably below 230° C., particularly preferably below 200° C.

Preference is likewise given to odorous substances which have a high volatility. The vapor pressure can be employed as a measure of the volatility. For the purposes of the present invention, a volatile odorous substance preferably has a vapor pressure of more than 0.001 kPa (20° C.). The odorous substance is more preferably a readily volatile compound or mixture. The odorous substance particularly preferably has a vapor pressure of more than 0.01 kPa (20° C.), more preferably a vapor pressure of more than 0.05 kPa (20° C.). Particular preference is given to the odorous substances having a vapor pressure of more than 0.1 kPa (20° C.).

Examples in which a chemical reaction can take place in the presence of the metal organic framework of the invention are the alkoxylation of monools and polyols. The method of carrying out such alkoxylations is described in WO-A 03/035717 and WO-A 2005/03069. The porous metal organic framework of the invention can likewise be used for epoxidation and for preparing polyalkylene carbonates and hydrogen peroxide. Such reactions are described in WO-A 03/101975, WO-A 2004/037895 and US-A 2004/081611.

Particular preference is given to catalytic reactions.

In addition, the metal organic framework of the invention can be used as support, in particular as support of a catalyst.

EXAMPLES

Example 1

Preparation of an Al-Terephthalic Acid MOF Using Sulfasalazine as Auxiliary 4.88 g of $AlCl_3*6H_2O$, 5 g of terephthalic acid and 2.99 g of sulfasalazine are suspended in 300 ml of DMF in a glass flask. The mixture is heated to 130° C. while stirring and maintained under these conditions for 18.5 hours. The product obtained is filtered off and washed with 3×50 ml of DMF and 4×50 ml of methanol. The product is subsequently transferred to a paper thimble and extracted with boiling methanol in an extraction apparatus for 120 hours. The product is finally dried at 100° C. in a vacuum drying oven for 24 hours. The yield is 4.12 g.

Figure 2:
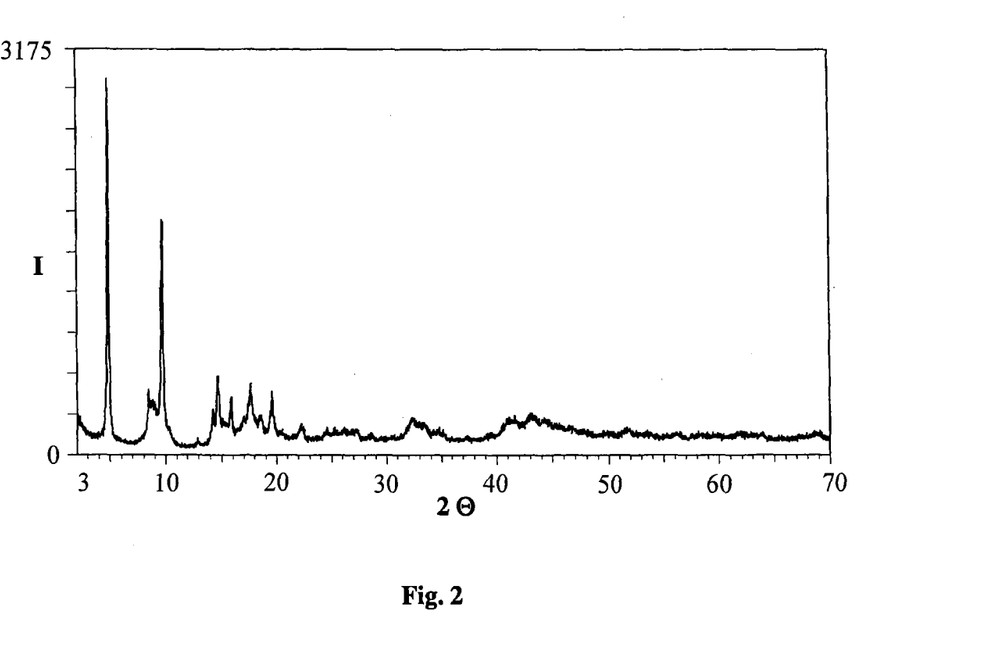
FIG. 2 shows the X-ray diffraction pattern of the aluminum terephthalate of the invention. The intensity I(Ln(Counts)) is shown here as a function of the 2-theta scale (2Θ).

The XRD (X-ray diffraction pattern) is shown in FIG. 2. Reflections are found at 2Θ=about 5°, about 10° and about 15° which are not observed in the conventional Al-terephthalate MOF (MIL-53). A novel structure is therefore present. The surface area is 1679 $m^2/g$. This is likewise higher than the known surface area values for MIL-53 (up to 1500 $m^2/g$). According to elemental analysis, the product comprises 11.6% by weight of Al, 44.2% by weight of carbon, 2.8% by weight of hydrogen, 0.7% by weight of $N_2$ and only 0.15% by weight of sulfur which originates as impurity from the auxiliary.

Example 2

Preparation of an Al-Terephthalic Acid MOF Using Calconcarboxylic Acid as Auxiliary 4.88 g of $AlCl_3*6H_2O$, 5 g of terephthalic acid and 3.3 g of calconcarboxylic acid are suspended in 300 ml of DMF in a glass flask. The mixture is heated to 130° C. while stirring and maintained under these conditions for 18 hours. The product obtained is filtered off and washed with 3×50 ml of DMF and 4×50 ml of methanol. The product is subsequently transferred to a paper thimble and extracted with boiling methanol in an extraction apparatus for 120 hours. The product is finally dried at 110° C. in a vacuum drying oven for 72 hours. The yield is 4.34 g.

The product displays the same reflections in the X-ray diffraction pattern (XRD) as example 1. The surface area is 1594 $m^2/g$. According to elemental analysis, the product comprises 10.0% by weight of Al, 46.1% by weight of carbon, 3.7% by weight of hydrogen, 3.2% by weight of $N_2$ and only 0.07% by weight of sulfur.

Example 3

Adsorption of $CO_2$ and CO

Adsorption isotherms for CO and $CO_2$ are measured in the range from 0 to 1.2 bar on a sample of about 200 mg in each case using the commercially available instrument ASAP 2420 (from Micromeritics). The measurement temperature is 40° C. The samples are pretreated at 200° C. under vacuum conditions (turbomolecular pump) for a number of hours before the measurement in each case.

Figure 3:
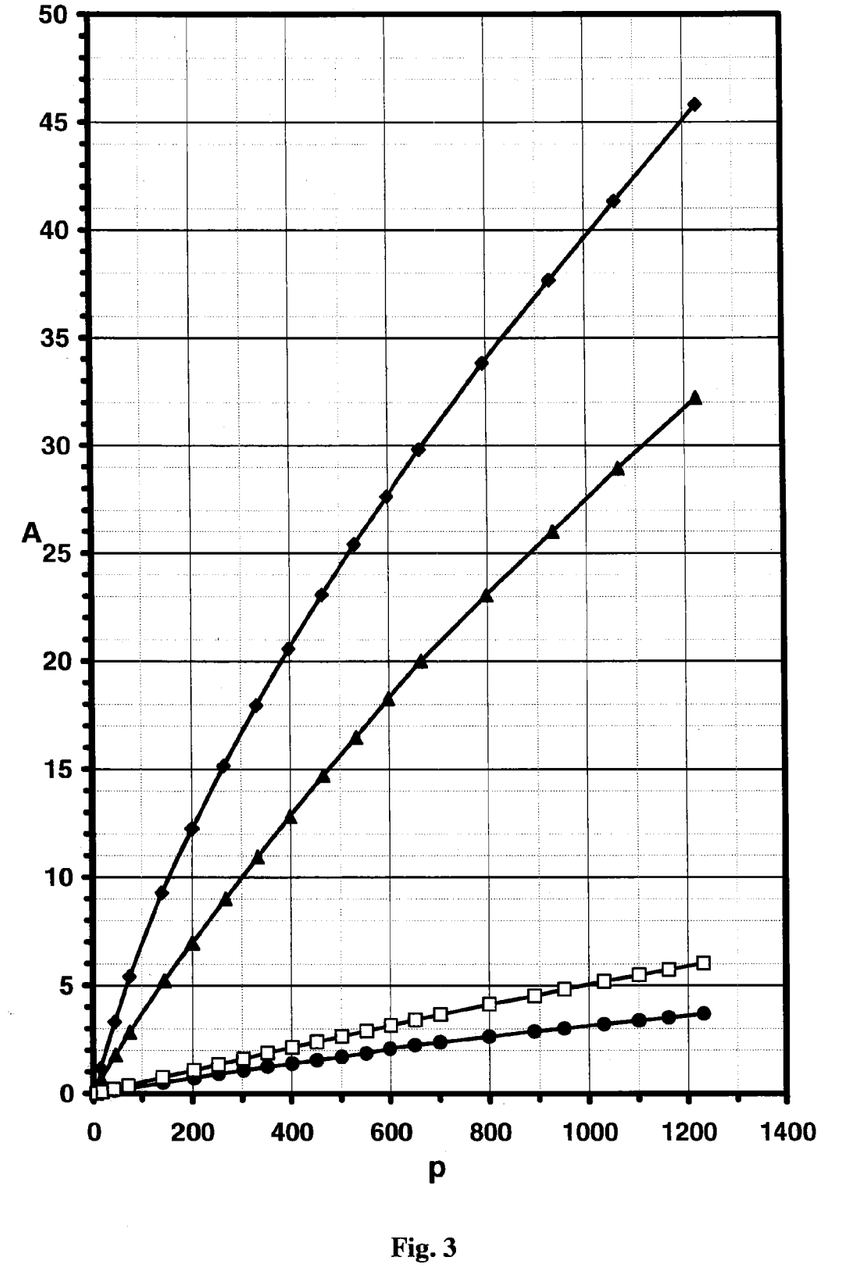
FIG. 3 shows curves for the adsorption of carbon dioxide and carbon monoxide on an aluminum terephthalate framework according to the invention and an aluminum terephthalate framework known from the prior art.

FIG. 3 shows the respective isotherms in comparison with Al-terephthalic acid from the prior art. The figure shows the gas uptake A (in standard ml/g) as a function of the pressure p (in mbar).

Samples measured are a sample as per example 1 (curve denoted by triangles: $CO_2$ adsorption; curve denoted by circles: CO adsorption in FIG. 3) and an Al-terephthalic acid MOF having the "MIL-53" structure from the prior art prepared as described in example 12 of WO-A 2007/023 134 (curve denoted by solid squares: $CO_2$ adsorption, curve denoted by open squares: CO adsorption in FIG. 3).

The overall flatter adsorption isotherms for the material according to the invention correlate with a lower adsorption energy, so that less energy is required for regeneration of the material after adsorption (e.g. in the desorption phase in a pressure swing adsorption). In addition, the relative difference between the $CO_2$ capacity and the CO capacity is helpful since this corresponds to a higher selectivity and thus higher achievable purities for a separation of $CO_2$ from CO.

The invention claimed is:

1. A process for preparing a porous metal organic framework comprising a bidentate organic compound coordinated to a metal ion selected from the group consisting of Al, Fe and Cr, wherein the bidentate organic compound is obtained from a dicarboxylic acid; the framework has a structure of which projection along [001] has a pattern; and each side of a hexagon in the pattern is bounded by a triangle, comprising reacting a reaction mixture comprising at least one compound of a metal selected from the group consisting of Al, Fe and Cr and the bidentate organic compound or a salt thereof in the presence of an auxiliary having at least one deprotonatable group in an organic solvent at a predetermined temperature and a predetermined pressure.

2. The process of claim 1, wherein the auxiliary has a molar mass in the range from 140 to 1000 g/mol.

3. The process of claim 1, wherein the auxiliary is 3,5-dihydroxybenzoic acid, 2,5-dihydroxybenzoic acid, mucic acid, glutamine, 4-sulfamoylbenzoic acid, 2-mercaptonicotinic acid, calconcarboxylic acid or sulfasalazine.

4. The process of claim 3, wherein the metal is Al.

5. The process of claim 1, wherein the metal is Al and the bidentate organic compound is terephthalic acid.

6. The process of claim 1, wherein the bidentate organic compound is obtained from a benzene dicarboxylic or naphthalenedicarboxylic acid.

7. The process of claim 1, wherein a X-ray diffraction pattern of the framework has a main reflection in the range 4°<2Θ<6°.

8. A method for uptaking at least one substance, comprising contacting the substance with a porous metal organic framework comprising a bidentate organic compound coordinated to a metal ion selected from the group consisting of Al, Fe and Cr, wherein the bidentate organic compound is obtained from a dicarboxylic acid; the framework has a structure of which projection along [001] has a pattern; and each side of a hexagon in the pattern is bounded by a triangle.

9. The process of claim 8, wherein the metal ion is Al.

10. The process of claim 8, wherein the metal ion is Al and the bidentate organic compound is terephthalic acid.

11. The process of claim 8, wherein a X-ray diffraction pattern of the framework has a main reflection in the range 4°<2Θ<6°.

12. A method for uptaking at least one substance, comprising contacting the substance with a shaped body comprising a porous metal organic framework, wherein the porous metal organic framework comprises a bidentate organic compound coordinated to a metal ion selected from the group consisting of Al, Fe and Cr, wherein the bidentate organic compound is obtained from a dicarboxylic acid; the framework has a structure of which projection along [001] has a pattern; and each side of a hexagon in the pattern is bounded by a triangle.

13. The process of claim 12, wherein the metal ion is Al.

14. The process of claim 12, wherein the metal ion is Al and the bidentate organic compound is terephthalic acid.

15. The process of claim 12, wherein a X-ray diffraction pattern of the framework has a main reflection in the range $4° < 2\Theta < 6°$.

* * * * *